United States Patent [19]

Sanders

[11] Patent Number: 4,907,602
[45] Date of Patent: Mar. 13, 1990

[54] DEVICE FOR CONTROLLING THE GLOTTIC OPENING

[75] Inventor: Ira Sanders, New York, N.Y.

[73] Assignee: The Mount Sinai School of Medicine of the City of New York, New York, N.Y.

[21] Appl. No.: 42,440

[22] Filed: Apr. 24, 1987

Related U.S. Application Data

[63] Continuation-in-part of Ser. No. 788,748, Oct. 18, 1985, abandoned.

[51] Int. Cl.$^4$ .............................................. A61N 1/32
[52] U.S. Cl. ..................................... 128/787; 128/421
[58] Field of Search ................... 128/419 R, 642, 774, 128/780, 782-784, 786-787, 791, 799

[56] References Cited

U.S. PATENT DOCUMENTS

| 4,334,542 | 6/1982 | Takinishi et al. | 128/787 |
| 4,351,330 | 9/1982 | Scarberry | 128/787 |
| 4,553,549 | 11/1985 | Pope et al. | 128/787 |

OTHER PUBLICATIONS

Sanders et al. (I), "Transcutaneous Electrical Stimulation of the Recurrent Laryngeal Nerve. A Method of Controlling Vocal Cord Position," Otolaryngology Head & Neck Surgery, vol. 95, No. 2, pp. 152-157, Sep. 1986.
Sanders et al. (II), "Transcutaneous Electrical Stimulation of the Recurrent Laryngeal Nerve in Monkeys," Otol, Rhino, & Laryngol, vol. 96, No. 1, Jan-Feb. 1987.
Sanders et al. (III), "Transtracheal/Transeosophageal Stimulation of the Recurrent Laryngeal Nerve," Presented at Meeting of West. Sec. of Amer. Laryngol., Rhinolog. and Otolog. Soc., Los Angeles, Cal., Jan. 10, 1987.
Philip H. Vogel, "The Innervation of the Larynx of Man and the Dog," Amer. J. Anatomy., vol. 90, pp. 427-442, 1952.
Bjorn-Erik Erlandson et al., "Intravaginal Electrical Stimulation, Clinical Experiments on Urethral Closure," Scand. J. Urol. Nephrol. (Suppl.) 44 (part III):-31-41, 1978.
Magnus Fall et al., "Long-Term Intravaginal Electrical Stimulation in Urge and Stress Incontinence," Scand. J. Urol. Nephrol. (Suppl.) 44 (part VI): 55-63, 1978.

*Primary Examiner*—William E. Kamm
*Attorney, Agent, or Firm*—Brumbaugh, Graves, Donohue & Raymond

[57] ABSTRACT

A method and devices for transcutaneous or transmucosal stimulation of the recurrent laryngeal nerve are provided. Recurrent laryngeal nerve stimulation is delivered by applying electric charge from an electrode in the form of a probe or an indwelling device to the intact neck skin at specific points along the tracheoesophageal groove or to mucosa within the esophagus, larynx, or trachea. In accordance with the present invention vocal cord excursion is related to frequency of the electrical stimulus.

4 Claims, 2 Drawing Sheets

DEVICE FOR CONTROLLING THE GLOTTIC OPENING

BACKGROUND OF THE INVENTION

This application is a continuation-in-part of application Ser. No. 788,748 filed Oct. 18, 1985.

The present invention relates to a method and device for controlling the glottic opening and airway in animals. Controlling the opening and closing of the vocal cords, and hence the airway, by way of a simple non-invasive technique and device therefor has far-reaching implications, not only in the field of otolaryngology, but also in the fields of anesthesiology and emergency medicine as well.

Direct stimulation of the recurrent laryngeal nerve (RLN) results in a characteristic movement of the vocal cords that is frequency dependent. In 1961, Nakamura in a paper entitled "Movement of the Larynx Induced By Electrical Stimulation of The Laryngeal Nerves" presented at the Upstate Medical Center of the State University of New York, in Syracuse, N.Y., May 29--June 3, 1961, and published in Brewer, *Research Potentials in Voice Physiology*, pages 129-136, N.Y. State University Press, 1964, demonstrated that in situ bilateral electrical stimulation of the RLN at a frequency of 20 Hz resulted in vocal cord abduction, while stimulation at frequencies greater than 40 Hz resulted in vocal cord adduction and a closed glottis. However, inasmuch as the experiments were conducted on dogs which were under operation with an exposed RLN and anesthetized, the clinical significance of these results remained obscure. To date clinical application of direct RLN stimulation has been proposed solely to aid surgeons in locating that nerve so that inadvertent damage of it can be avoided during surgery.

At the present time there is no easy method of controlling vocal cord position for diagnostic or therapeutic purposes. Current techniques involve mechanical methods such as pushing the vocal cord to assess arthritis or blowing increased air pressure through the larynx in cases of laryngospasm to attempt opening of the glottis. Transcutaneous or transmucosal stimulation of the RLN has not previously been proposed as a method for controlling vocal cord position in lieu of the methods described above. Yet, transcutaneous or transmucosal stimulation of nerves in other areas of the body is an established and consistently used therapeutic tool. See, e.g. Scand. J. Urol. Nephrol. (Suppl.) 44, pp. 31-41 and 55-63 (1978). Such stimulation has also been used, for example, by neurologists as a method for alleviating pain and as a means for diagnosing disorders of the spinal cord and peripheral nervous systems. In addition, physiatrists have utilized transcutaneous or transmucosal stimulation to facilitate muscle reeducation.

SUMMARY OF THE INVENTION

In accordance with the present invention, it has been found that transcutaneous or transmucosal electrical stimulation of the RLN, through intact skin or mucosa in the region of the larynx, results in a controlled, graded opening and closing of the airway. The invention was surprising, since it was not evident from studies on exposed laryngeal nerves that the recurrent laryngeal nerve could be stimulated selectively transcutaneously or transmucosally.

Thus, it is a primary object of the invention to provide a method for transcutaneous or transmucosal stimulation of the recurrent laryngeal nerve (RLN). A principal aspect of the invention is to provide a method for reliably controlling the movement of the vocal cords which results in the opening and closing of the airway.

Another principal objective of the invention is to provide a device for controllably opening and closing the glottis and to test the glottal mechanism comprising a means for applying a periodic electrical stimulus at a predetermined anatomical location, the stimulus having a frequency which evokes a predetermined amount of stimulation in at least one intrinsic laryngeal muscle and having a current effective to selectively stimulate the recurrent laryngeal nerve or a portion thereof.

A still further aspect of the invention is an indwelling device for controllably stimulating the glottic opening of an animal which comprises a soft platform having a first and second surface. The platform conforms to the hypopharynx and proximal esophagus wherein the first surface fits over and contacts the laryngeal and esophageal mucosa, respectively. Alternatively, the platform conforms to the trachea and laryngeal lumen with the first surface fitting over and contacting the lumenal mucosa. plurality of electrodes is attached to and spaced over the first surface of the platform. Leads are attached to the electrodes and to a means for generating an electrical stimulus. The electrical stimulus so generated has a frequency selected to evoke a predetermined amount of stimulation in at least one laryngeal muscle and has a current effective to selectively stimulate at least a portion of the recurrent laryngeal nerve.

In application to human medicine, the method and devices of the present invention offer important diagnostic tools for use in laryngoscopy. The method and devices therefor may be used to differentiate between an arthritic or paretic vocal cord, for prognostic indication in cases of RLN trauma, and to assess vocal cord motion, for example, in the evaluation of tumor. By direct muscle stimulation, response of vocal cord and arytenoid movement can b assessed. Selection of appropriate stimuli will, for example, detect denervated muscle. Other uses would be readily evident to physicians and include applications in the fields of anesthesiology and emergency medicine. The abducting function could assist in difficult intubations and in overcoming laryngospasm. The adductor function can be used to close the glottis if a patient regurgitates during intubation or extubation, thereby allowing time for suctioning and preventing aspiration. In awake patients who are able to tolerate this technique and device therefor, additional applications and uses are possible.

The present invention has been tested on male mongrel dogs and on monkeys. Transcutaneous RLN activation in these species has been shown to be a safe and effective way to mobilize the vocal cords. The implications for human medical practice are evident.

In accordance with the method of the present invention, the points of electrical stimulation can be at one or more of the following anatomical sites: (1) through intact neck skin along the tracheoesophageal groove; (2) through the tracheal wall posterolaterally; (3) through the esophageal wall anterolaterally; (4) anterior to the esophagus at the level of the cricoid; (5) lateral to the arytenoid; (6) deep in the pyriform fossa; (7) directly on the vocal cord itself; (8) on the false cord and aryepiglottic fold; and (9) between the arytenoids. The required current, frequency of pulse and precise location are determined by the physician in accordance with the needs and limitations of the patients. In general, the frequency is selected to provide a desired control over the extent of the glottic opening and the current is controlled to selectively stimulate the recurrent laryngeal nerve. When stimulating the entire main trunk of the RLN at anatomical sites (1)-(3) mentioned above, the motion of the vocal cords is dependent on the frequency of the applied current, with abduction generally occurring at or below 30 Hz and adduction above 40 Hz.

Transcutaneous stimulation of the RLN in humans must be approached carefully. As an evolutionary adaptation allowing man to speak, the larynx is found in a more inferior position in the neck relative to other species. The segment of RLN accessible for stimulation is therefore much smaller in humans than in other species. In addition, in man a greater amount of tissue, including a larger thyroid gland, is interposed between the skin surface and RLN. Humans may therefore require greater stimulus amperages to activate the RLN.

Transesophageal and transtracheal approaches to RLN stimulation have now been developed and applied successfully in dogs. "Transtracheal/Transesophageal Stimulation of the RLN" I. Sanders, J. Aviv, and H. F. Biller presented at the Western Section Meeting of the Triological Society Jan. 9-11, 1987, Los Angeles, Calif. The RLN runs its course in close proximity to the esophagus and trachea and can be readily activated by means of a stimulating probe inserted via the mouth and wedged laterally into either the anterior esophageal wall or posterior tracheal wall where transmural stimulation produces frequency-dependent vocal cord motion. Ready access to the RLN is provided while, at the same time, the need to traverse the thyroid is avoided.

At the criocothyroid joint, which is located immediately superior to the region where the probe is inserted into the anterior esophageal wall, the RLN bifurcates, sending a superficial branch to the posterior cricoarytenoid muscle (PCA), an abductor muscle. An additional approach, encompassed by the present invention, involves transmucosal stimulation of this branch of the RLN across the overlying laryngeal mucosa by passage of current applied with a blunt probe to activate only the branch to the PCA. Since the PCA is an abductor muscle, such stimulation results only in abduction, regardless of stimulus frequency.

Thus, in order to evaluate denervated muscle, the present invention can be used to stimulate points other than those found in the main trunk of the RLN. Muscle tissue which has a live nerve supply will typically respond to square wave stimulation. For example, stimulation of denervated muscle requires a high current of about 20 milliamps which is 10 times more current than required for innervated muscle when square wave pulses are used.

Muscle with a live nerve supply will not, however, normally respond to triangular wave stimulation having a slowly rising wave form. This is apparently because muscles having a live nerve supply accommodate to the slowly rising triangular wave form without contracting. On the other hand, denervated muscle uniquely responds to triangular wave stimulation. In this way disorders of the nerve supply to the various intrinsic laryngeal muscles can be diagnosed by direct application of triangular wave stimulation to the muscles.

Since RLNs are found on both the left and right of the trachea, the invention may be practiced by stimulating either one or both of these nerves. Results can be obtained even when only one of the nerves is stimulated.

The transesophageal and transmucosal approaches described above require the use of a probe to be inserted through the mouth to stimulate the RLN. Transtracheal stimulation of the RLN is performed by means of a probe inserted in the mouth or by passing the probe through an existing tracheostomy. Transtracheal stimulation can also be accomplished by passing a thin probe through the cricothyroid membrane into the trachea and then stimulating the posterior tracheal wall.

Also encompassed within the scope of the present invention is an indwelling electrode device, referred to herein as the larynx electrode platform (LEP), which is inserted via the mouth and is designed to rest on the anterior wall of the hypopharynx and proximal esophagus. This device overlies the laryngeal and anterior esophageal mucosa, respectively. Alternatively the LEP is designed to conform to the trachea and laryngeal lumen and overlie the lumenal mucosa. The LEP reliably and discretely delivers current across the appropriate regions of the laryngeal, esophageal, or trachael mucosa.

A device such as the LEP precisely conforms to the topography of the hypopharynx or trachea and provides effective anchoring, positioning, electrode-target coupling, and stimulus targeting.

In addition, the indwelling device preferably meets the following design parameters:
1. Atraumatic—Easy to insert and remove, no damage to mucosa when left in place.
2. Unobtrusive—No interference with physician's visualization of vocal cords or movement of arytenoids.
3. Stable—Position stays constant despite swallowing and cough of patient.
4. Consistent—Same results obtainable over multiple trials.
5. Conformity—Shape corresponds exactly to complex posterior laryngeal anatomy of each patient.
6. Efficiency—Electrode placements on device should be at exact spots of maximal excitation of RLN and PCA.

DETAILED DESCRIPTION OF THE INVENTION

Figure 1:
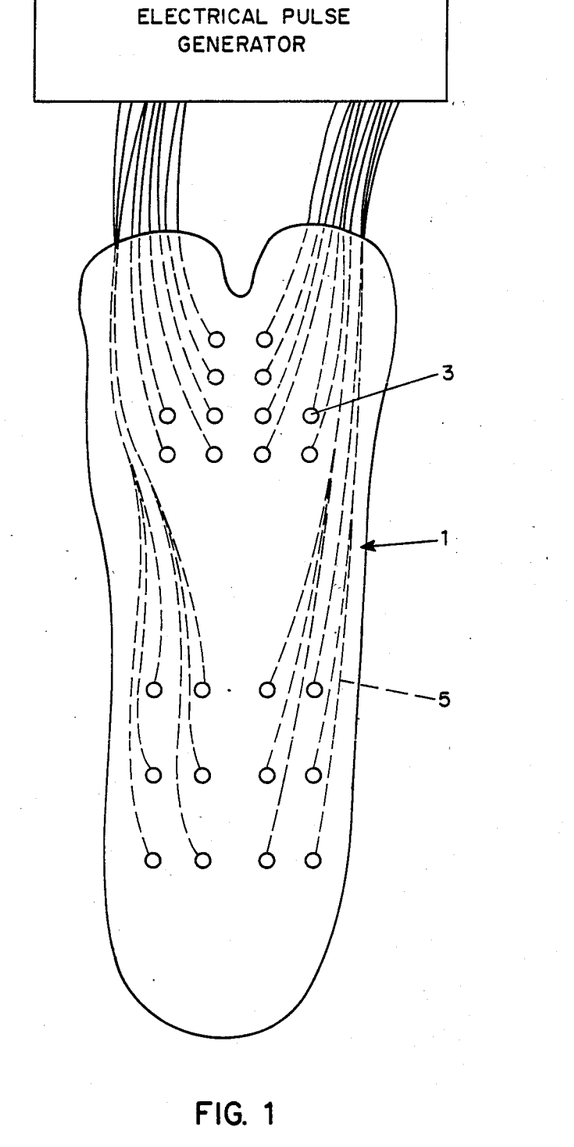
FIG. 1 is the indwelling device for controllably stimulating the glottic opening of an animal according to the invention.

The indwelling device, for controllably stimulating the glottic opening of an animal comprises a soft platform which conforms to and fits over the hypopharynx and proximal esophagus and fits over and contacts the laryngeal and esophageal mucosa respectively. In other designs the platform confirms to the trachea and laryngeal lumen and fits over and contacts the lumenal mucosa. The platform 1 has a plurality of electrodes 3 securely attached to and spaced over the surface of the platform 1. The electrodes are preferably made of metal or some other physiologically acceptable conductive material. Lead wires 5 are attached to each electrode and are suitable for attachment to means for generating an electrical stimulus. The lead wire 5 is made from any physiologically acceptable conductive metal, preferably insulated aluminum wire.

The unique method of constructing the (LEP) indwelling device comprises the steps of forming an in vivo mold of either the patient's hypopharynx and proximal esophagus or tracheal and laryngeal lumen; constructing a plaster cast from the mold; producing a soft platform, using the cast as a template, of the anterior wall of either the hypopharynx and esophagus or the tracheal and laryngeal lumen; and studding the surface of the resulting platform with electrodes. The mold is made using conventional impression material for example material by dentists for constructing dental impressions. The cast can be made of any suitable material, preferably plaster. As a result of this process a unique custom-fitted, soft, pliable, indwelling platform is produced which conforms precisely to the complex anatomy of the hypopharynx or the trachea and is embedded with a plurality of electrodes which are located on the platform to correspond to the mucosal imprints from the in in vivo mold. This method of electrode placement enables discrete and efficient delivery of electrical stimulation to the target tissue.

If the indwelling LEP is not used, the device for controllably stimulating the glottic opening comprises means for applying a periodic electrical stimulus at a predetermined anatomical location. Such means for applying the electrical stimulus is preferably an electrode in the form of a probe. The electrode is designated to carefully control the precise area of application of the stimulating current. If the current is supplied at a precisely controlled spot, a relatively small amount of current will be sufficient. Preferably the effective area of electrode contact is less than a circle of about 5 mm diameter. If the area of current transfer is larger, it will be necessary to supply a greater amount of current, which may be undesirable. Smaller diameter electrodes, i.e. 3 mm or less are more efficient. In studies where stimulation is carried out on animals, such as dogs, where the skin is stretched and highly resilient, a simple pointed electrode is suitable. In the preferred applications or for human medicine, it is contemplated, for example, that the electrode will be insulated to closely sheathe the tip of the electrode whereby contact between the electrode and surrounding skin or mucosal areas will be avoided.

In general, the electrodes can be of any conventional and convenient shape, i.e. circular, flat, etc. which are suited for physiological applications, for example a single electrode containing both a cathode and an anode. A flat edged electrode may have a better "feel", and be preferred by some. Where stimulation of the deep pyriform fossa is desired, a flat edged electrode is also preferred for ease of insertion. Where the electrode is inserted for stimulating the mucosa or muscles within the larynx, a bent tip is preferred to facilitate approach to the point of stimulation.

The present invention seeks to stimulate the recurrent laryngeal nerve transcutaneously or transmucosally. The location of the application of the electrode probe in accordance with the present invention produces varying effects. Stimulation of the main trunk of the RLN produces a frequency-dependent opening or closing of the vocal cords. In accordance with the present invention the main trunk may be stimulated through the intact skin of the neck by applying an electrode in the tracheoesophageal groove in the neck region, which lies generally between the sternal notch and the thyroid cartilage. Preferably, the RLN is accessed through the tracheal wall posterolaterally or through the esophageal wall anterolaterally as by use of the LEP or similar devices.

Stimulation at the locations discussed above appears to involve the main trunk of the RLN and is frequency specific. For example, animal studies have shown that frequencies of 30 Hz or below caused vocal cord opening while frequencies of 40 Hz to 100 Hz caused vocal cord closing.

Other locations for application of the electrode probe in accordance with the present invention involve terminal branches of the RLN, such as the branch to the PCA, and are not frequency specific. Therefore, specific muscle movement can be elicited to aid in diagnosis of muscle response or for other purposes. Even though the response is not frequency specific, however, the extent of response is frequency dependent. Stimulation with a low frequency (i.e. 10–20 Hz) will produce a lesser response (abduction or adduction depending on the muscle) than will a higher frequency stimulus (i.e. 70–90 Hz). Locations where non-frequency specific response is found are the anterior esophagus (posterior cricoarythenoid), lateral to the arytenoid (transversal arytenoid), between the arytenoid (interarytenoid), deep in the pyriform fossa (lateral cricoarytenoid, thyroarytenoid), directly on the vocal cord itself (thyroarytenoid), on the false cord and aryepiglottic fold (aryepiglottic). Except for the stimulation point in the pyriform fossa, each of these points is on muscle tissue of a single intrinsic laryngeal muscle. However, the stimulus applied probably triggers the terminal nerve tissue within the muscle, which, in turn, causes muscle contraction.

In general the electrodes in probes method to stimulate the RLN in each of these locations are blunt and on long thin handles with a bend near the end to allow approaching the target from an angle. It is preferred that a probe used to reach the anterior esophagus at the level of the cricoid, contain a flat edge electrode mounted on a thin guide which can fit into the esophagus and help maintain contact.

Electrical stimulation can be provided to either the electrode probe or the LEP by any electrical generator of the type generally known to be suitable for nerve stimulation. Very broadly, any alternating current will serve the purpose; however, it is also generally recognized that cathodic stimulation is more effective than anodic stimulation. Accordingly, the preferred electrical stimulation is provided by a generator which will provide a cathodic pulse of a controlled duration, for example from 0.01 to 10 milliseconds at recurring intervals selected in accordance with the needs of the user.

In animal studies, when stimulating the main trunk of the RLN, vocal cord abduction occurs generally at lower frequencies, i.e., in the range of 10 to 40 Hz, while the maximal closure of the glottic opening occurs at higher frequencies, typically in the range of 50 to 80 Hz and preferably above 60 or 70 Hz. In human applications it is expected that the same general frequency ranges will be applicable; however, the frequencies at which maximal opening or maximal closure are obtained may vary from the frequencies of the maximal responses observed in the animal studies.

It is also important, particularly in human medicine, to carefully control the current of the stimulating pulse. Particularly when applying electrical stimulation in the neck area, care must be taken to stimulate only the desired nerve and to avoid stimulation of other areas. Many parts of the nervous system originate in the cerebral center and descend through the neck. The technique of the present invention depends on stimulating the RLN, transcutaneously or transmucosally, but not other parts of the nervous system in the same region. For example, nerves known to be associated with the cardiovascular system pass through the neck region and if improperly stimulated catastrophic results will ensue.

The present invention is surprising because it has been found that transcutaneous or transmucosal stimulation can be effectively controlled to selectively and discretely stimulate the recurrent laryngeal nerve without having any significant effect on the other nervous pathways throughout the neck region. For this reason, however, it is important to limit the current of the stimulation. The current applied should be sufficient to produce the desired response in one or more of the intrinsic laryngeal muscles, but not more than sufficient. In animals having a relatively thick skin, such as dogs, it has been found that a current in the range of 10 milliamps is sufficient to produce the desired response. In thin skinned animals, such as monkeys, 1 milliamp is sufficient to produce a good response. In human applications the preferred current range appears to be up to 20 mAmps, and will vary depending upon the physical condition of the patient involved.

It should be noted that the amount of stimulation current is, to some extent, inversely related to the pulse duration. Particularly at very short pulses, i.e. less than ½ msec., increased current per pulse will be required.

The following examples illustrate the use of both electrode probes and LEP in the practise of the invention but are not meant to limit the scope of the invention.

EXAMPLE 1

Six healthy male mongrel dogs, weighing between 17 and 20 kg, were studied. All six dogs were prepared in the following manner: The dogs were anesthetized with sodium pentobarbital (30 mg/kg IV) and placed in the supine position with the neck shaved from clavicle to mandible and maximally extended.

A vaginal speculum was used to visualize the larynx without restricting movement of the vocal cords. A 20 G needle was inserted through the epiglottis and skin of the neck and secured in position by a clamp in order to maintain an unobstructed view of the vocal cords and arytenoids. A measuring rod with millimeter gradations was placed in the mouth and extending up to the vocal cords, but without touching the vocal cords. This allowed direct measurement of vocal cord excursion in millimeters. Pentobarbital was titrated so that upon inspiration and expiration vocal cord movement was less than 1 mm.

Conducting jelly (Signa Gel, Parker Laboratories, Inc., Orange, N.J.) was placed in a thin film beginning at the sternal notch and extending superiorly approximately 8 cm along the TE (tracheoesophageal) groove bilaterally. An electrical stimulator (Electronics For Medicine, White Plains, N.Y.) was used to deliver square wave cathodal pulses. The anode was clamped to the left buccal mucosa and the cathode was clamped to an 8 cm freer elevator, which served as the stimulator rod.

The tip of the freer elevator was firmly invaginated into the TE groove beginning at the sternal notch and moving superiorly to approximately 4-8 cm above the sternal notch and held in place. Care was taken not to have the skin on either side of the tip of the stimulating rod touch, as this would disperse the current. 10 mA of current was delivered, in 1 msec pulses at a pulse rate of 30 Hz, with the vocal cords under direct visual observation, to define the motor point where maximal ipsilateral vocal cord excursion took place.

Figure 2:
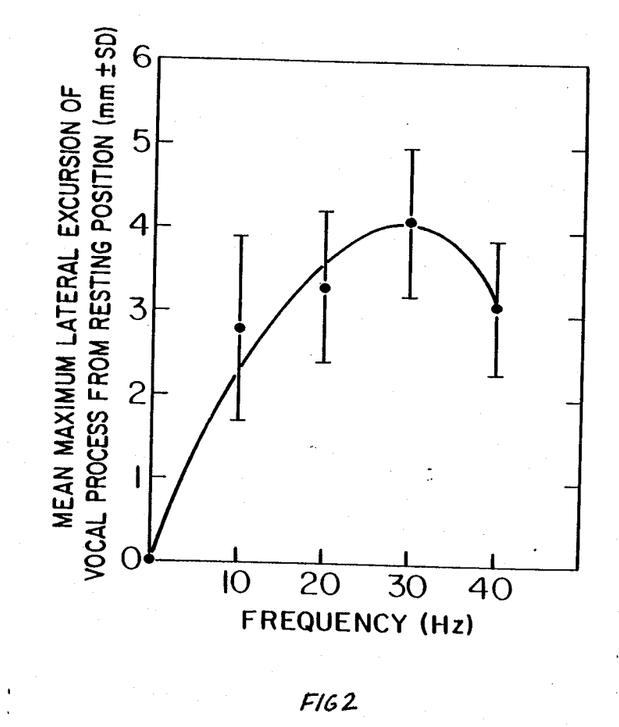
FIG. 2 is a graph showing mean maximal lateral excursion of the vocal process from resting position as a function of the frequency of electrical stimulus.
Figure 3:
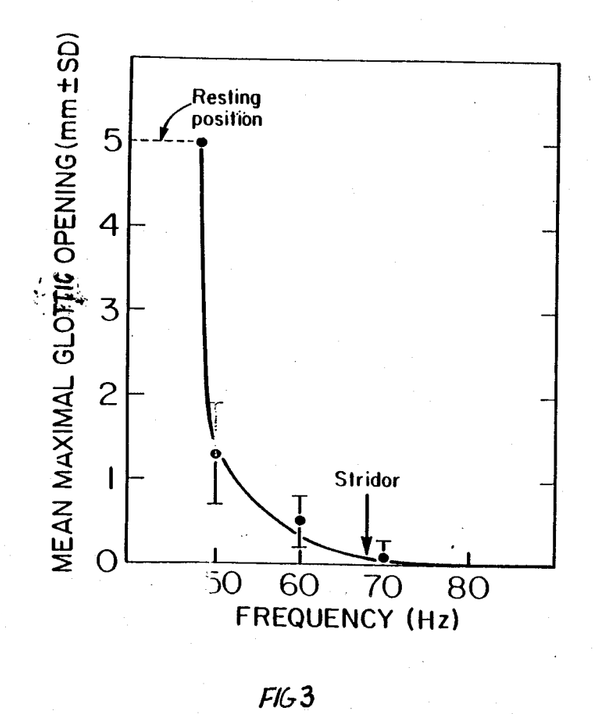
FIG. 3 is a graph showing mean maximal glottic opening as a function of the frequency of electrical stimulus.

The stimulator machine was then switched to deliver a train of pulses. In order to avoid measurement variation associated with variations of the vocal cord during inspiration and expiration, all measurements were made upon inspiration. A 10 mA current was delivered in pulse trains with a duration of 1 msec/pulse beginning at a frequency of 10 Hz and increasing in 10 Hz increments to 100 Hz. The resultant movement of the vocal cords was measured and recorded by direct vision, photographs and videotape. Both the right and the left RLN's were transcutaneously stimulated. The results are reported graphically for stimulation of the left RLN FIGS. 2 and 3.

Measurement of vocal cord excursion was divided into two groups, cord abduction (movement at frequencies between 0-40 Hz) and cord adduction (movement at frequencies greater than 50 Hz). For each group, cord movement was measured as follows: Cord abduction (0-40 Hz)—Maximum lateral excursion of ipsilateral vocal process from its resting position at inspiration. Cord adduction (>50 Hz) Distance between ipsilateral and contralateral vocal processes, i.e., the maximum diameter of the glottic opening.

Stimulation at 10 Hz caused gross vocal cord vibration from resting position to about 50% of the completely abducted position. At 20 Hz cord vibrations became finer with the lateral excursion of oscillation approaching maximal abduction. At 30 Hz the vocal process became stable at maximal abduction, although fine twitching of the thyroarytenoid (TA) muscle could still be observed. Increasing the stimulus frequency to 40 Hz caused mild medial bowing of the TA and a slight shift of the arytenoid in comparison to 30 Hz, however the vocal process maintained near maximal abduction. At frequencies greater than 40 Hz these changes became progressively more evident with the entire vocal cord moving medially despite the vocal process being in a lateral abducted position.

At frequencies of 50 Hz the bowing of the TA invariably brought it into contact with the contralateral vocal cord. The arytenoids often made contact at this frequency. However, the lateral displacement of the vocal process maintained a diamond shaped opening in the center of the glottis. At 60 Hz the above changes were more evident, and the dogs usually displayed mild stridor. At 70 Hz all of the dogs demonstrated severe, loud stridor with no visible airway. Increasing the frequency further tightened the already closed airway with some dogs progressing to complete airway obstruction.

EXAMPLE 2

Each of five adult, male dogs weighing between 17 and 20 kg was anesthetized with sodium pentobarbital, 30 mg/kg IV, and positioned supine on an examining table. The epiglottis was retracted by pinning it to the thyrohyoid membrane.

A 3 mm wide wad of gauze with a strand of 0 Vicryl suture attached thereto was moistened and advanced 5 cm into the esophagus with packing forceps. The gauze served to block the flow of impression material into the distal esophagus.

25 g of alginate powder (L. D. Caulk Company, Milford, Del.) were mixed with 50 cc ice water, forming the impression material. This pasty mixture was quickly spatulated into a Toumey syringe which had been modified by cutting its tip at an oblique angle so that the flow of impression material could be better directed. Each dog's mouth was held open and the tongue retracted anteriorly to enable direct visualization of the superior larynx. With its opening facing posteriorly, the syringe spout was positioned just posterior and inferior to the mucosa overlying the posterior-superior rim of the cricoid cartilage. By angling the syringe tip posteriorly and positioning its opening downward, the glottic aperture was avoided. The impression material was then injected into the area and the alginate was allowed to set for two minutes. The resulting hardened mold of the hypopharynx and proximal esophagus was retrieved by withdrawing the wad of gauze and forcing the mold outward.

The mold was then rinsed and sunk into a plaster of Paris base. The portion of the mold that had contacted the anterior wall was facing upward. The plaster base was then encircled with a wax wall to form a well with the algiate mold at its center. Stone plaster was poured into the well and the resulting plaster cast was allowed to harden, thereby forming a mirror image of the portion of the mold which had contacted the anterior esopageal wall.

The cast was trimmed using a sanding wheel, and a hole was drilled in the region corresponding to the esophageal wall. Using a vacuum press (Omnivac V Vacuum Adapter, Omnidental Corp., Harrisburg, Pa.), a 55 $cm^2$ sheet of 0.15 gauge vinyl (Dentiform, Inc., Harveys Lake, Pa.) was heated and drawn over the cast to form a vinyl platform. The esophageal hole in the cast provided improved suction.

The platform was then trimmed as follows: The superior border of the impression was cut horizontally just superior to the imprint of the interarytenoid mucosa. A "V" notch was made to accommodate for the posterior glottic aperture, extending inferiorly to the imprint of the interarytenoid notch. The vinyl was cut inferiorly in order to extend 5 cm into the esophagus, as measured from the imprint of the cricopharyngeus mucosa. The superior-lateral borders of the platform were cut so as to extend only as far as the area corresponding to the pyriform sinuses. The inferior-lateral borders were trimmed to include a portion of the convexity of the region corresponding to the anterior esophageal wall.

Electrodes made of a conductive material suitable for physiological use were blanketed over the area of the vinyl impression which was to overly the PCA by using the mucosal imprints of this muscle as a guide. Preferably the electrodes were made of metal or other physiologically acceptable conductive material and were embedded in the surface of the platform. Electrode leads were prepared from 30 cm segments of 30 gauge insulated aluminum wire, each stripped to expose 6 mm of one end. This bare portion was wound into a loop of 1 mm diameter in a plane perpendicular to direction of the wire. The loop-hole was then filled with solder. Lead wires attached to the electrodes were threaded through the vinyl and pulled taught so that the terminal loop lay flush with the latex surface. They were positioned 5 mm apart to form an array of about 16 electrodes over a 2.5 $cm^2$ area for each PCA.

Similarly, electrodes were spotted over the regions of the platform which were to overly the anterior-lateral esophageal walls. Using the imprint of the cricopharyngeus muscle as a landmark, electrodes were threaded at 5 mm intervals in a 4 $cm^2$ region on each side. Lead wires were labeled and secured with silicone adhesive material, for example, Silastic, to form the completed LEP.

EXAMPLE 3

The test animals used in Example 2 were reanesthetized and placed supine on the examining table. The epiglottis was pinned to the thyrohyoid membrane and the mouth stented open with a vaginal speculum to improve visualization of the vocal cords.

Each dog's customized LEP prepared according to Example 2 was inserted using packing forceps. Under direct vision, the resting glottic aperture was measured in milimeters. With the anode of a pulsatile stimulator (Electronics for Medicine, White Plains, N.Y.) clamped to the buccal mucosa and the cathode attached to the lead wire, each electrode was tested in turn.

Electrodes overlying the PCA were evaluated using an 80 Hz current. An amperage of 5 mA was applied, and cord abduction measured. The value for maximal abduction (MA), that is, the maximal width of the glottic aperture during unilateral stimulation, was recorded. Testing was repeated at 4 and 3 mA. The single electrode on each side which could attain MA at 3 mA was termed the "optimal electrode" (OE). The two OEs were then activated simultaneously at 10 mA, and the resulting glottic aperture was measured.

The array of electrodes overlying the anterior-lateral esophageal wall was then evaluated. Testing was performed at 5, 4, and 3 mA. Vocal cord adduction was noted when 80 Hz current was used. Electrodes were then evaluated at 30 Hz, and cord abduction measured. Again, left and right OEs were identified and activated simultaneously at 80 Hz, 10 mA, to determine if total glottic closure could be achieved.

The LEP was then removed, rinsed and reinserted. The OEs were retested to determine if they could consistently attain MA at 3 mA.

In all trials, the tone of the adjacent laryngeal muscles was noted in order to determine if they were being inadvertently stimulated. After removal of the LEP, the laryngeal and esophageal mucosa were inspected for evidence of abrasion.

No mucosal abrasion was noted in any of the test dogs. In all dogs tested the vocal cords could be clearly visualized, and access to them was unimpeded.

The aginate molds could be fashioned with ease, speed and accuracy. The plaster casts produced from them captured with great detail not only the anatomical contours of the region, but also the complex infoldings of the mucosa. The vinyl impressions made from the plaster templates also displayed striking detail, and the mucosal imprints were an effective aid in placing the electrodes on the LEP.

The customized LEP for each of the five experimental animals was quickly and easily inserted, snugly fitting into this highly contoured region. Vertical and lateral displacement of the LEP was prevented by its invagination into the pyriform sinuses and its cupping of the posterior cricoid convexity. The V-notch enabled unobstructed air flow through the glottic aperture. Each LEP appeared to lay flush against the adjacent mucosa, and moved in unison with the larynx during swallowing.

As shown in Table I, each of the five LEPs was able to achieve excellent PCA control.

TABLE I

| | PCA STIMULATION APERTURES* | | | |
|---|---|---|---|---|
| | RESTING APERTURE | UNILATERAL STIMULATION APERTURE (mm) | | BILATERAL STIMULATION APERTURE |
| DOG | (mm) | RIGHT | LEFT | (mm) |
| 1 | 4.0 | 7.5 | 7.5 | 10.0 |
| 2 | 4.5 | 7.5 | 8.0 | 10.5 |
| 3 | 4.5 | 8.5 | 8.0 | 11.0 |
| 4 | 4.0 | 7.0 | 7.0 | 10.5 |
| 5 | 5.0 | 9.0 | 8.5 | 12.0 |

*PCA stimulation results using the optimal electrodes. The values are glottic apertures in mm.

About half of the PCA electrodes on each side stimulated the neural branch, as evidenced by ispilateral vocal cord abduction. At 5 mA, up to three electrodes on each side yielded maximum ipsilateral abduction (MA). At 3 mA, only one electrode per side, termed the "optimal electrode" (OE), yielded MA. When the PCA-OEs for both left and right sides were activated simultaneously, bilateral cord abduction resulted, dramatically augmenting the glottic aperture as compared with the resting aperture. No adjacent laryngeal muscles were noted to tense or contract upon activation of the PCA-OEs.

Main trunk RLN excitation was attained in two of the five LEPs, by activating electrodes in the esophageal array. In these two, activation of the esophageal OE at 3 mA produced ipsilateral vocal cord abduction at 30 Hz, and ipsilateral adduction at 80 Hz. When esophageal OEs from both left and right sides were activated simultaneously at 10 mA. 80 Hz, bilateral adduction occurred, resulting in total glottic closure and airway occlusion. For the other three LEPs, main trunk control was less dramatic, and neither maximal abduction nor complete closure was achieved.

Removal and reinsertion of each LEP resulted in the same electrodes being identified as the optimal electrodes.

EXAMPLE 4

After testing each dog with its own LEP, each was tested using the other four LEP's prepared according to Example 2. The OEs on each device were identified for all five dogs.

When any one dog was tested with one of the other four LEPs, the PCA-OEs always were found to be either identical to or lie just adjacent to the original PCA-OEs. Thus any LEP could be used to optimally stimulate any of the dogs by activating either the original PCA-OE or any of the four electrodes immediately adjacent to it, comprising an active zone of about 1 cm² around each original PCA-OE.

This type of interchangeability was not demonstrated for the esophageal OEs.

In all trials, the tone of the adjacent laryngeal muscles was noted in order to determine if they were being inadvertently stimulated. After removal of the LEP, the laryngeal and esophageal mucosa were inspected for evidence of abrasion. No mucosal abrasions were noted in any of the test dogs. In all of the test animals, the vocal cords were clearly visualized, and access to them was unimpeded.

The design objectives considered in the development of the LEP were evaluated through the test of the five LEPs described in Example 2-4 above. The soft vinyl LEP was atraumatic to the laryngeal mucosa, causing no abrasion of the mucosa. The LEP was unobstrusive in its location, and, because it was indwelling, allowed unimpeded access to the glottis. Since the LEP cupped tightly the cricoid prominence and pyriform sinuses, it remained stably anchored throughout the duration of lengthy experiments. Furthermore, the device was positioned in the same location upon reinsertion, as indicated by the consistent identity of the optimal electrodes (OEs).

Effective mucosal contact was indicated by the efficiency of stimulation. Maximal abduction could be achieved using as little as 3 mA current, which is known to be the same amperage required for probe stimulation in this region. Thus, the LEP's precise replication of anatomical contours had enabled efficient electrode-to-target coupling.

For the PCA electrode array, excellent targeting resulted. In all five LEPs, an optimal electrode was identified which would reliably activated the PCA and thereby achieved maximal cord abduction. Bilateral activation of the left and right PCA's yielded a greatly enlarged glottic aperture.

Reliable targeting of the main-trunk RLN using the esophageal array was achieved in only two of the LEPs. In these, complete glottic closure was attained. Inadequate targeting in the other three possibly was a result of the variable position of the RLN in this region, and of the ability of the RLN to move outside the target area when the neck is moved.

The results, furthermore, indicated that an LEP fashioned from one dog can be used effectively in any dog of similar size (17 to 20 kg in this experiment). The ability to interchange LEPs indicates that for dogs of a given size, the topography of the target region is similar. That is, relative positioning and contour of the pyriform sinuses, cricoid convexity, and upper esophagus are nearly the same. This interchangeability enhances the potential clinical utility of the LEP. It is conceivable, for example, that an LEP constructed from a human cadaver would be functional in a human of similar size.

Previous studies of electrical current applied across human vaginal mucosa have shown that stimulus amperages of up to 30 mA cause no mucosal damage. Since the current used in this study was 10 mA or less, no mucosal injury would be expected and none was seen.

AN EXPLANATION OF THE INVENTION

The following theory of the involved muscles is offered by way of an explanation of the invention and reflects the observations which have been made in the course of the animal studies. It should be understood, however, that this is a theory which is advanced and is not intended as a limitation on the scope of invention claimed.

On the basis of the test results described above as well as other observations that have been made, it is believed that the frequency dependent movement of the vocal cords is due to the different contraction times of the intrinsic abductor and adductor muscle groups. Muscles consist of fast twitch and slow twitch fibers with the response of the entire muscle being a reflection of the relative proportions of the two fiber groups. The term "contraction time" quantifies the speed of muscle contraction and is a direct measurement of the time necessary for a resting muscle to shorten to its smallest length when a single supramaximal electrical stimulus is applied.

In comparison to other skeletal muscles, the intrinsic laryngeal muscles are all considered fast twitch, but some are faster than others. The adductor muscles (primarily the lateral cricoarytenoid (LCA) and the (TA) have an average contraction time of 15 msec which makes them second only to the extraocular muscles (9 msec) with respect to speed of contraction. This fast contraction time probably evolved in response to needs for a rapid laryngeal protective reflex and because of the unique demands of phonation. The abductor muscle (the posterior cricoarytenoid (PCA)) functions mostly in the comparatively slower movements of the respiratory cycle. Their contraction time of 30 msec is double that of the adductors.

These antagonistic muscle groups are both supplied by the same nerve, the recurrent laryngeal (RLN). When an electrical impulse is applied to the RLN, all of the axons are stimulated synchronously. As the motor axons in the RLN are all about the same diameter, these action potentials are delivered to both muscle groups and simultaneously initiate a contraction.

Using these facts, it then follows that for every electrical pulse delivered to the RLN, both muscle groups will begin their contractions at the same time and pull against each other for the first 15 msec. After this point, it is believed that the adductors are no longer developing force, and instead are overcome by the pull of the abductors which continue generating force for another 15 msec. After these 30 msec of activity, the abductors also relax and the cycle repeats itself upon arrival of the next pulse.

What would be expected, in an idealized situation where both muscle groups generate identical force, is a vocal cord which briefly tenses in place and then swings open, only to return to its resting position. The experimental situation differs from the ideal in that the adductors contain more muscle fibers than the abductors, and are therefore capable of generating more force.

As an illustrative example, consider what happens at a frequency of 10 Hz. The one msec electrical pulse is delivered to the RLN every 100 msec. According to the above theory, of this 100 msec interval, contraction of both muscle groups for 15 msec would be expected, then unopposed contraction of the abductor group for an additional 15 msec would be expected. Following these 30 msec of activity, there should be approximately 70 msec where no activity takes place until the next pulse occurs. Indeed, this theoretically predicted movement of the vocal cord corresponds to the direct observation seen in the dogs studied.

At 30 Hz, pulses are delivered every 33 msec, which approximates the PCA's 30 msec contraction time. Since the PCA cannot relax between pulses at this frequency, an almost continuous tonic contraction would be expected. Furthermore, in laryngeal muscles, the forces developed at tonic contraction summates to levels as high as ten times an isolated twitch. Since the adductors are still contracting for only 15 msec out of every cycle and are relaxing for the remainder, we would expect the vocal cord to be steadily abducted at 30 Hz. Again, direct observation confirms this theoretical expectation.

At frequencies greater than 30 Hz, the PCA does not develop any additional force, as it is already in a state of tonic contraction generating maximal force. The adductor group, however, continues developing more force at higher frequencies as the muscles are being temporally recruited. For example, at 70 Hz, pulses are delivered every 14 msec, so that the adductors will be fused into a tonic contraction. Since the adductor muscles contain more muscle fibers than the abductors, have better leverage on the arytenoid, while now also at force summation, one would expect to see a closed glottis once both groups are simultaneously in tonic contraction.

The foregoing summation of a theoretical explanation is based on the measurements which were made in the dog tests. Because of physiological demands believed to be responsible for the different contraction times in dogs are similar in human beings, it is suggested the human vocal cord motion will also be frequency dependent, although as noted at the outset of this disclosure, the precise frequency of maximal responses may vary from those stated above.

CLINICAL USES

As discussed above, the method and devices described herein have numerous potential clinical use. A safe, functional LEP according to the present invention has several potential clinical applications especially in testing for neuromuscular function or in positioning the vocal cords for therapy as in laser treatment. For example, the LEP may be used during laryngoscopy, to abduct the cords to provide access to an infraglottic lesion, thereby facilitating laser surgery. It may also have use as a diagnostic tool in distinguishing vocal cord paralysis from cricoarytenoid arthritis. For example, applying current across the PCA mucosa would induce cord motion in the former case, but not in the latter.

In addition, the LEP may be of value to the anesthesiologist. The LEP could be inserted after induction of general anesthesia. Just prior to intubation, the device could be activated to cause cord abduction, thereby minimizing cord abrasions from contact with the endotracheal tube. If the patient were to vomit during extubation, the LEP could be used to close the glottis, thereby preventing aspiration. Vomitus overlying the airway could then be suctioned and the airway reopened by an abducting stimulus. Finally, recent experiments have demonstrated that the LEP can be used to break experimentally-induced laryngospasm in dogs.

The LEP should be able to remain in place for extended periods of time, thus providing for other clinical uses. In the chronically-intubated patient, for example, pressure ischemia from continuous contact between the endotracheal tube and the vocal process causes tissue necrosis and scarring. If the vocal cords could be periodically abducted away from the tube by use of the LEP or a variant thereof, the resultant transient restoration of circulation could reduce ischemic injury. The LEP also provides a means for manipulating the glottic aperture which offers a variety of clinical possibilities.

In addition, the mold-making technology developed for forming the LEP itself has potential clinical applications. During a diagnostic laryngoscopy for a suspected laryngeal neoplasm, a mold of specific areas of the posterior larynx could be made. An impression fashioned from this mold could then be used as a prosthesis in subsequent reconstructive head and neck procedures.

Other uses of the method and devices described herein relate to airway control. Preferred devices for such use include laryngeal probes and combining the LEP with other probes.

In one embodiment, a variant of the LEP is combined with a nasogastric tube or esophageal stethoscope for airway control. These are tube-like devices which are normally passed into the esophagus during the course of a general anesthesia. By adjusting such tubes to the correct distance, the electrodes would thus be properly placed. Stimulation of the RLN at a frequency to cause abduction, or stimulation of the branch to the PCA could open the vocal cords to aid intubation. If the electrodes were to be placed near the main trunk of the RLN, stimulation at a frequency which causes adduction would close the cords, thereby allowing time to suction material present in the hypopharynx if the patient vomits during induction.

The LEP also can aid in intubation by attaching an LEP to an endotracheal tube in an analogous fashion to the attachment of a bayonet to a rifle. In adults, the endotracheal tube is sealed after insertion by blowing up a balloon at one end of the tube. When intubating a patient, even if the larynx isn't seen, the leading edge of the LEP could slip into the trachea and help guide the end of the endotracheal tube to a proper position just above the vocal cords. The position of the electrodes on the LEP are placed so that when resistance is felt as the end of the endotracheal tube touches the closed cords, the electrodes on the LEP would be directly under the PCA such that a momentary stimulation would open the vocal cords. The anesthesiologist sensing the loss of resistance could then slide the tube into the trachea atraumatically. Moreover, since resistance giving way can be felt during stimulation of the RLN branch to the PCA, one could be relatively sure the trachea was being intubated and not the esophagus. Esophageal intubation is a frequent cause of anxiety during intubation procedures and an occasional cause of death and could be made easier if the tube were used in combination with an LEP.

An additional advantage of this embodiment is that the attachment of the endotracheal tube to the LEP would allow placement of the endotracheal tube balloon in proper position to lift the tube away from the posterior part of the glottic airway, thereby reducing the risk of rubbing of the tube in this area which is an occasional cause of laryngeal scarring.

At the present time, adult endotracheal tubes are sealed by blowing up a balloon at the end of the tube. When the tube is in place a long time, as commonly practiced in intensive care patients on ventilators, the balloon stretches and damages the trachea.

A solution to this problem involves an endotracheal tube with one long or two shorter balloons. One balloon (sealing balloon), is located in the position of currently used endotracheal tube balloons. However, a second balloon, (reservoir balloon), is located to fit between the vocal cords. During inspiration, when ventilatory pressure is at its peak, the vocal cords are stimulated by means of a probe or indwelling device (LEP) or electrode directly on the reservoir balloon, thereby closing the vocal cords on the reservoir balloon. After inspiration, when pressure is low, the air then flows back into the reservoir balloon. In accordance with the present invention, the periodic opening and closing of the vocal cords by controlled stimulation of the main trunk of the RLN or the thyroarythenoid muscle through its under-surface prevents the mucosal necrosis and tracheal stretching currently seen with long term endotracheal use.

A further variation of the above device involves use of a single balloon in the larynx extending from the vocal cords to the cricoid. The reservoir part of the balloon would be located between the vocal cords and the sealing part at the cricoid. The cricoid location has an advantage as a sealing area because, unlike the trachea, it is not distensible. This is seen as a disadvantage in currently used endotracheal devices since a balloon which is blown up in this area is almost certain to cause necrosis of the mucosa and eventual scarring. However, in a dynamic system using periodic controlled opening and closing of the vocal cords, an interval of high pressure during peak inspiration is balanced by an interval three times as long during expiration. Thus, blood flow is permitted thereby allowing complete recovery of the mucosa. The device could probably function indefinitely.

A still further variation is to locate the sealing balloon right between the vocal cords. Dog experiments have shown that stimulation of the vocal cords in accordance with the invention results in up to 120 mmHg pressure. This is two to three times as much pressure as needed to seal the trachea during ventilation. The vocal cords themselves would, therefore, clamp down on a balloon and create a seal without the need of another balloon in the system.

Adapting an endotracheal device as described above in accordance with the present invention for pediatric airway control provides even greater benefit. Endotracheal tubes for young children do not contain balloons for sealing because the airway in children is so small that the lumen of the tube must be as large as possible for effective ventilation. A seal is attained by direct contact of the outer surface of the endotracheal tube with the cricoid mucosa. Although the pediatric tubes are made from a soft material, the sealing contact is traumatic to the mucosa, especially in repeated intubations, and can lead to serious complications. Pediatric airway control effected by controllably opening and closing the vocal cords in accordance with this invention can provide a way of reducing or eliminating damage to the tracheal mucosa.

The LEP can also be combined with other airway control devices to control vocal cord mobility. For example, an LEP could be combined with an esophageal obturator airway to control vocal cord position in emergency airway control situations.

Possible airway control applications of the present invention also encompass transtracheal stimulation in addition to transesophageal approaches. Airway control using transtracheal stimulation combined with an LEP or other such device according to the present invention involves formation of a seal around an inserted endotracheal tube by stimulation-induced closing of the vocal cords.

The foregoing method, device and procedure for making the device are illustrative of those currently preferred. Many modifications of the method of the invention, the device therefor, and procedure for making a device according to the invention will be apparent to those skilled in the art and hence, what is specifically disclosed is not intended to limit the scope of the invention claimed hereinbelow.

I claim:

1. A device for the controllably stimulating the glottic opening of an animal comprising a soft indwelling platform having a first and second surface, which platform conforms to the hypopharynx and proximal esophagus, the first surface fitting over and in contact with the laryngeal and anterior esophageal mucosa, a plurality of electrodes attached to and spaced over the first surface of the platform, and leads attached to each of the electrodes, said leads being attachable to means for generating and applying an electrical current to the leads.

2. A device as described in claim 1, further comprising means for generating an electrical current to the leads such that the electrodes produce an electrical stimulus, wherein the electrical stimulus has a frequency which is selected to evoke a predetermined amount of stimulation in at least one laryngeal muscle and a current effective to selectively stimulate at least a portion of the recurrent laryngeal nerve.

3. A device for controllably stimulating the glottic opening of an animal comprising a soft indwelling platform having a first and second surface, which platform conforms to the trachea and laryngeal lumen, the first surface fitting over and in contact with the luminal mucosa, a plurality of electrodes attached to and spaced over the first surface of the platform, and leads attached to each of the electrodes, said leads being attachable to means for generating and applying an electrical current to the leads.

4. A device as described in claim 3, further comprising means for generating an electrical current to the leads such that the electrodes produce an electrical stimulus, wherein the electrical stimulus has a frequency which is selected to evoke a predetermined amount of stimulation in at least one laryngeal muscle and a current effective to selectively stimulate at least a portion of the recurrent laryngeal nerve.

* * * * *